United States Patent
Chang et al.

(10) Patent No.: US 9,881,845 B1
(45) Date of Patent: Jan. 30, 2018

(54) ELECTRONIC DEVICE, LID STRUCTURE AND PACKAGE STRUCTURE

(71) Applicant: Advanced Semiconductor Engineering, Inc., Kaohsiung (TW)

(72) Inventors: Yung-Yi Chang, Kaohsiung (TW); Hsun-Wei Chan, Kaohsiung (TW); Ching-Han Huang, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 0 days.

(21) Appl. No.: 15/291,971

(22) Filed: Oct. 12, 2016

(51) Int. Cl.
 *H01L 27/14* (2006.01)
 *H01L 23/055* (2006.01)
 *G01N 27/12* (2006.01)
 *G01N 33/00* (2006.01)

(52) U.S. Cl.
 CPC ......... *H01L 23/055* (2013.01); *G01N 27/125* (2013.01); *G01N 33/0027* (2013.01)

(58) Field of Classification Search
 CPC . G01N 27/125; G01N 33/0027; H01L 23/055
 See application file for complete search history.

(56) References Cited

U.S. PATENT DOCUMENTS

| | | | |
|---|---|---|---|
| 8,852,513 B1* | 10/2014 | Speer ................... | H01L 23/055 204/424 |
| 2005/0178186 A1* | 8/2005 | Gollar, III .......... | G01N 27/4045 73/31.05 |
| 2008/0283989 A1* | 11/2008 | Jeung ................... | H01L 23/055 257/682 |
| 2015/0075258 A1* | 3/2015 | Paik ..................... | G01N 27/041 73/31.06 |

* cited by examiner

*Primary Examiner* — Yosef Gebreyesus
(74) *Attorney, Agent, or Firm* — Foley & Lardner LLP; Cliff Z. Liu (57) ABSTRACT

An electronic device includes a transducer including a sensing area and a covering structure that covers the transducer. The covering structure includes a shelter portion and defines at least one aperture. The shelter portion covers the sensing area. The aperture includes a first curved surface and a second curved surface farther away from the sensing area than the first curved surface, and a first center of a first curvature of the first curved surface is at a different location than a second center of a second curvature of the second curved surface.

21 Claims, 12 Drawing Sheets

ELECTRONIC DEVICE, LID STRUCTURE AND PACKAGE STRUCTURE

BACKGROUND

1. Field of the Disclosure

The present disclosure relates to the field of electronic devices, lid structures and package structures, and more particularly to electronic devices, lid structures and package structures having an aperture for air to flow through.

2. Description of the Related Art

A gas sensor may have a sensing area for sensing a concentration of a gas to be tested. However, moisture or particulates may affect sensitivity of the gas sensor.

SUMMARY

In one or more embodiments, an electronic device includes a transducer including a sensing area and a covering structure that covers the transducer. The covering structure includes a shelter portion and defines at least one aperture. The shelter portion covers the sensing area. The aperture includes a first curved surface and a second curved surface farther away from the sensing area than the first curved surface, and a first center of a first curvature of the first curved surface is at a different location than a second center of a second curvature of the second curved surface.

In one or more embodiments, a lid structure includes a main body including a shelter portion and defining at least one aperture surrounding the shelter portion. Each aperture has a first surface and a second surface opposite to the first surface, and a first center of a first curvature of the first surface is at a different location than a second center of a second curvature of the second surface.

In one or more embodiments, a package structure includes a carrier, a die including a sensing area disposed adjacent to a surface of the die, and a covering structure attached to the carrier. The covering structure forms an accommodating space that accommodates the die. The covering structure includes a shelter portion and defines at least one aperture. The shelter portion covers the sensing area. The aperture includes a first curved surface and a second curved surface farther away from the sensing area than the first curved surface, and a first curvature of the first curved surface is greater than a second curvature of the second curved surface.

DETAILED DESCRIPTION

To protect a sensing area of a sensor on a substrate of a gas sensor device, a cap or lid can be used to cover the sensor and to contact the substrate to form an accommodating space. The cap or lid can define an aperture above the sensor, such that gas to be tested enters the accommodating space through the aperture and then contacts the sensing area, and then the sensing area of the sensor can sense the concentration of the gas to be tested. However, a single aperture can result in low sensitivity because of, for example, low gas flow. Further, when the single aperture is over a center of the sensor area, particles in a surrounding environment can contact and contaminate the sensing area.

To address these concerns, the cap or lid can be designed to define different kinds of patterns or types of apertures. However, in different designs, a path length that a gas entering the accommodating space follows, through the various apertures, can differ, which can result in a low reaction efficiency of the sensing area. In addition, a complicated pattern or type of aperture can make manufacturing more difficult.

To address the above concerns, the present disclosure provides an improved electronic device having a cap or lid with a shelter portion and at least one aperture. In one or more embodiments, the shelter portion can cover or overlie a sensing area, and the aperture can have a first curved surface close to the sensing area and a second curved surface farther away from the sensing area than the first curved surface. A first center of a first curvature of the first curved surface is at a different location than a second center of a second curvature of the second curved surface. The shelter portion may cover the sensing area so as to keep the sensor area from being contaminated. Further, the aperture may have a convex and a concave border (e.g., substantially kidney shaped), which can correspond to a large aperture space, and this configuration can make manufacturing simpler or less costly than other configurations. In addition, path lengths of gas entering the accommodating space can be made substantially equal, which can result in a high reaction efficiency of the sensing area.

Figure 1:
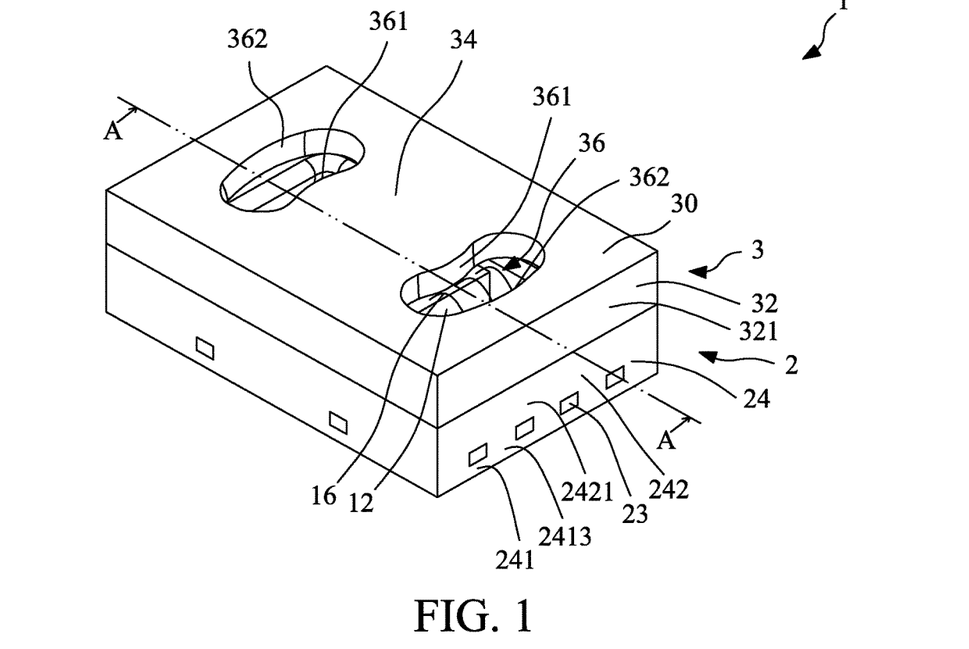
FIG. 1 illustrates a top perspective view of an electronic device according to one or more embodiments of the present disclosure.
Figure 2:
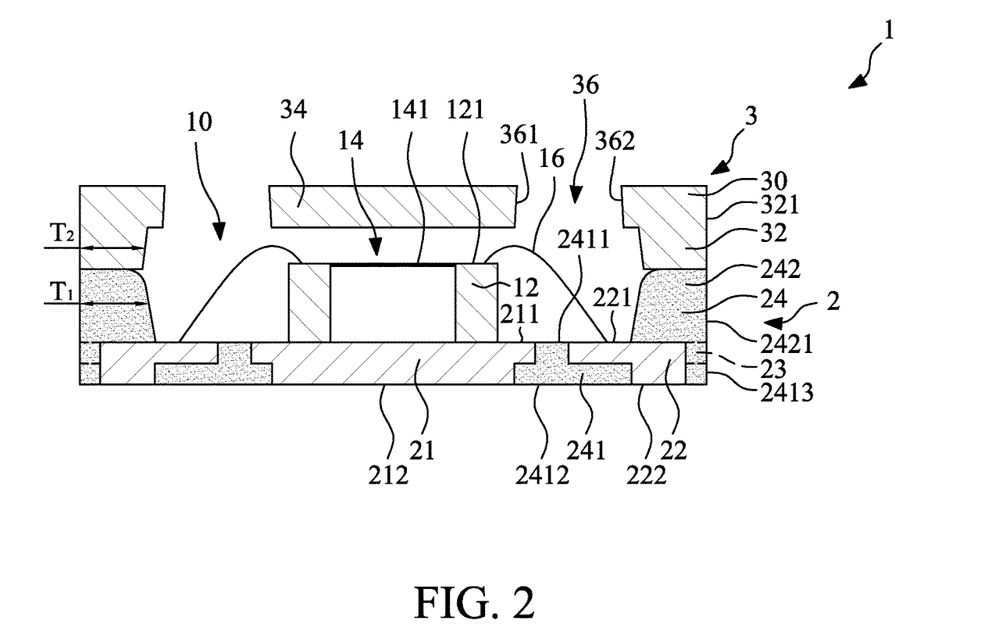
FIG. 2 illustrates a cross-sectional view taken along a line A-A of FIG. 1.

FIG. 1 illustrates a top perspective view of an electronic device 1 according to one or more embodiments of the present disclosure. FIG. 2 illustrates a cross-sectional view of the electronic device 1 taken along a line A-A of FIG. 1. In the illustration of FIGS. 1 and 2, the electronic device 1 may be a package structure, and can include at least one transducer 12, a carrier 2 and a covering structure 3. The transducer 12 can be a semiconductor die such as a sensor die, and can be disposed on and electrically connected to the carrier 2. The transducer 12 has a first surface 121, a sensing area 14 and a layer of metal oxide 141. The sensing area 14 is disposed adjacent to the first surface 121 of the transducer 12 in this embodiment, and the metal oxide 141 is disposed on the sensing area 14 in this embodiment. In one or more embodiments, the electronic device 1 may include multiple transducers 12, such as, for example, four transducers 12.

In the embodiment illustrated in FIGS. 1 and 2, the metal oxide 141 can be formed by applying an adhesive with metal oxide particles (e.g., stannic oxide ($SnO_2$) particles) dispersed on the sensing area 14, and then curing the adhesive so as to form the layer of metal oxide 141. In addition, the electronic device 1 may further include a heater (not shown). Examples of operation of the transducer 12 are described as follows. When a gas to be tested (e.g., carbon dioxide ($CO_2$) gas) contacts the metal oxide 141, a chemical reaction can occur. Negative oxygen ions of the metal oxide 141 can leave the metal oxide 141, and positive ions of the gas can attach to the metal ions of the sensing area 14. Meanwhile, an electron density in the sensing area 14 can be increased and a resistance of the sensing area 14 can be reduced. Thus, conductivity of the sensing area 14 will be increased. A concentration of the gas to be tested can influence the conductivity of the sensing area 14. A specific concentration of the gas to be tested can correspond to a specific amount of conductivity of the sensing area 14. Therefore, the concentration of the gas to be tested can be determined from a value corresponding to the conductivity of the sensing area 14 (for example, an output voltage of the transducer 12). It is noted that variation of the conductivity of the sensing area 14 can reflect the concentration of the gas to be tested, and a configuration of the transducer 12 can be adjusted for detecting a composition or kind of the gas to be tested. Different kinds of metal oxide 141 can be differently suited for sensing different kinds of gas to be tested. When the gas to be tested is removed, the sensing area 14 can be heated by the heater to a temperature in a range of approximately 200° C. to approximately 300° C. Thus, oxygen in surrounding air can combine with the metal ions of the sensing area 14 to form the metal oxide 141. That is, the metal oxide 141 assumes an initial state again.

The carrier 2 can receive the transducer 12. The carrier 2 can be a leadframe and can include a die paddle 21, leads 22, connecting bars 23 and an encapsulant 24. A first portion 241 of the encapsulant 24 can be disposed between the die paddle 21 and the leads 22, such that the die paddle 21 and the leads 22 are insulated from each other. A second portion 242 of the encapsulant 24 can be disposed on the leads 22 to form a supporting wall. As shown in FIG. 2, a first surface 211 of the die paddle 21, a first surface 2411 of the first portion 241 of the encapsulant 24 and a first surface 221 of the lead 22 can be substantially coplanar. The first surface 211 of the die paddle 21 and the first surface 221 of the lead 22 can be exposed from the first surface 2411 of the first portion 241 of the encapsulant 24. A second surface 212 of the die paddle 21, a second surface 2412 of the first portion 241 of the encapsulant 24 and a second surface 222 of the lead 22 can be substantially coplanar. The second surface 212 of the die paddle 21 and the second surface 222 of the lead 22 can be exposed from the second surface 2412 of the first portion 241 of the encapsulant 24. The transducer 12 can be disposed on (e.g., adhered to) the first surface 211 of the die paddle 21, and can be electrically connected to the first surface 221 of the lead 22 through one or more bonding wires 16. The second portion 242 (the supporting wall) of the encapsulant 24 can protrude from the lead 22 such that the supporting wall 242 supports the covering structure 3. A thickness $T_1$ of at least a portion of the second portion 242 (the supporting wall) can be, for example, greater than or equal to approximately 0.1 millimeters (mm), such as greater than or equal to approximately 0.15 mm, greater than or equal to approximately 0.18 mm or greater than or equal to approximately 0.2 mm.

The connecting bars 23 can connect the leads 22 of the electronic device 1 and the leads of a neighboring electronic device (not shown), for example, during a manufacturing process, and can remain as part of the electronic device 1 after a singulation process (e.g., cutting process). The connecting bars 23 can be exposed from an outer surface 2413 of the first portion 241 of the encapsulant 24. In one or more embodiments, the outer surface 2413 of the first portion 241 of the encapsulant 24 can be substantially coplanar with an outer surface 2421 of the second portion 242 (the supporting wall) of the encapsulant 24. The outer surface 2413 of the first portion 241 and the outer surface 2421 of the second portion 242 (the supporting wall) can form an outermost peripheral surface of the carrier 2. In one or more embodiments, the die paddle 21, the leads 22, and the connecting bars 23 can include similar or a same material (e.g., a metal, such as copper); and the encapsulant 24 can include a molding compound, such as epoxy.

The covering structure 3 can be attached to the carrier 2 to form an accommodating space 10 for accommodating the transducer 12, and can cover the transducer 12. As illustrated in FIGS. 1 and 2, the covering structure 3 can be a lid structure or a cap structure, and can include a main body 30 and at least one supporting wall 32. The main body 30 can have a shelter portion 34 and can define at least one aperture 36 adjacent to the shelter portion 34 or defining the shelter portion 34, possibly in combination with another one or more apertures, or surrounding the shelter portion 34, possibly in combination with another one or more apertures. The shelter portion 34 is substantially defined by the one or more apertures 36. The shelter portion 34 can be disposed above the sensing area 14 and can help to cover and protect the sensing area 14 from contamination. A size of the shelter portion 34 can be greater than a size of the sensing area 14 (e.g., a largest surface of the shelter portion 34 can have a larger surface area than a surface area of the sensing area 14). The aperture 36 can allow a gas to be tested to pass through, such that the gas to be tested can enter the accommodating space 10 through the aperture 36 and then contact the sensing area 14.

The aperture 36 can extend through the main body 30, and can have a first curved surface 361 and a second curved surface 362. The first curved surface 361 can be closer to the sensing area 14 than is the second curved surface 362. As depicted in FIGS. 1 and 2, the main body 30 can defines two apertures 36 that can be disposed on different sides of the shelter portion 34. The two apertures 36 can be symmetrical to each other, and the first curved surfaces 361 of the two apertures 36 can define at least a portion of the shelter portion 34.

The supporting wall 32 can extend vertically from a periphery of the main body 30. A thickness $T_2$ of at least a portion of the supporting wall 32 is greater than or equal to approximately 0.1 mm, such as greater than or equal to approximately 0.15 mm, greater than or equal to approximately 0.18 mm or greater than or equal to approximately 0.2 mm. The supporting wall 32 can have an outer surface 321 that is an outermost peripheral surface of the covering structure 3. The outer surface 321 of the supporting wall 32 can be substantially coplanar with the outer surface 2413 of the first portion 241 of the encapsulant 24 and the outer surface 2421 of the second portion 242 (the supporting wall) of the encapsulant 24 (the outermost peripheral surface of the carrier 2). The covering structure 3 and the carrier 2 can be formed by cutting simultaneously from both sides during the manufacturing process, or can be formed by a single cutting process. The outermost peripheral surface of the electronic device 1 can be a substantially flat surface. In one or more embodiments, a material of the covering structure 3 (the main body 30 and the supporting wall 32) can be plastic, and can be formed by injection molding.

As illustrated in FIGS. 1 and 2, the supporting walls 32 of the covering structure 3 can be attached to the second portion 242 (the supporting wall) of the encapsulant 24 of the carrier 2, such that the supporting walls 32 and the second portion 242 define the accommodating space 10. However, in one or more embodiments, the accommodating space 10 may be defined by the supporting wall 32 and not by the second portion 242, or by the second portion 242 and not by the supporting wall 32.

Figure 3:
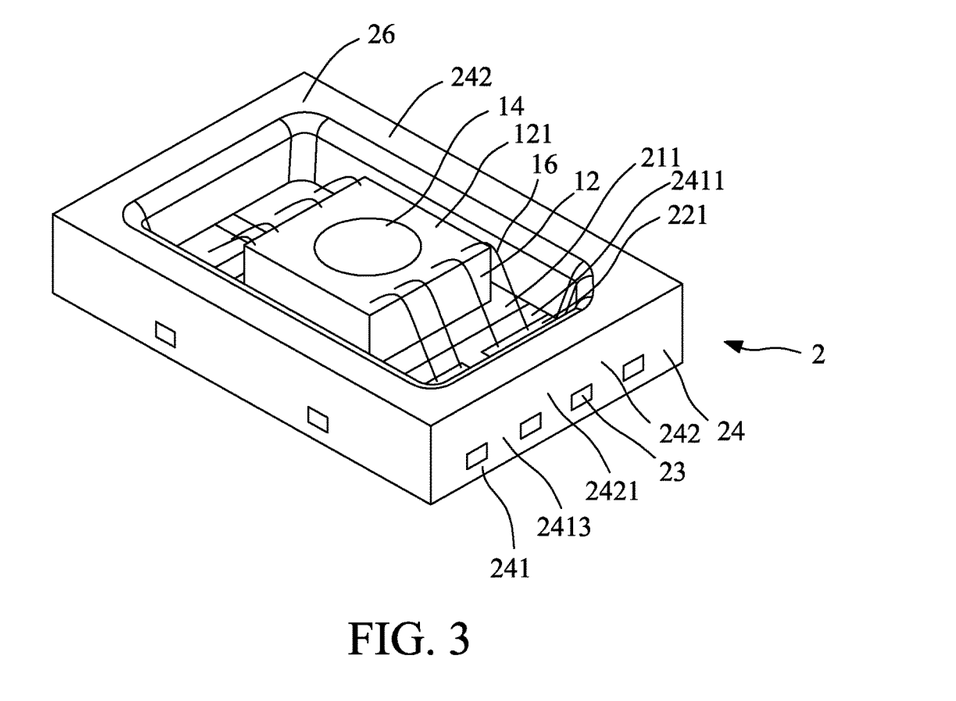
FIG. 3 illustrates a top perspective view of a carrier and a transducer depicted in FIG. 2 according to one or more embodiments of the present disclosure.

FIG. 3 illustrates a top perspective view of the carrier 2 and the transducer 12 of FIG. 2 according to one or more embodiments of the present disclosure. In FIG. 3, the covering structure 3 (FIGS. 1 and 2) is depicted as removed. The carrier 2 can include four second portions 242 (supporting walls), and a curved chamber portion 26 between each two second portions 242. This can help to facilitate manufacturing of the encapsulant 24. The curved chamber portion 26 can be disposed at a corner of the second portion 242 of the encapsulant 24.

Figure 4:
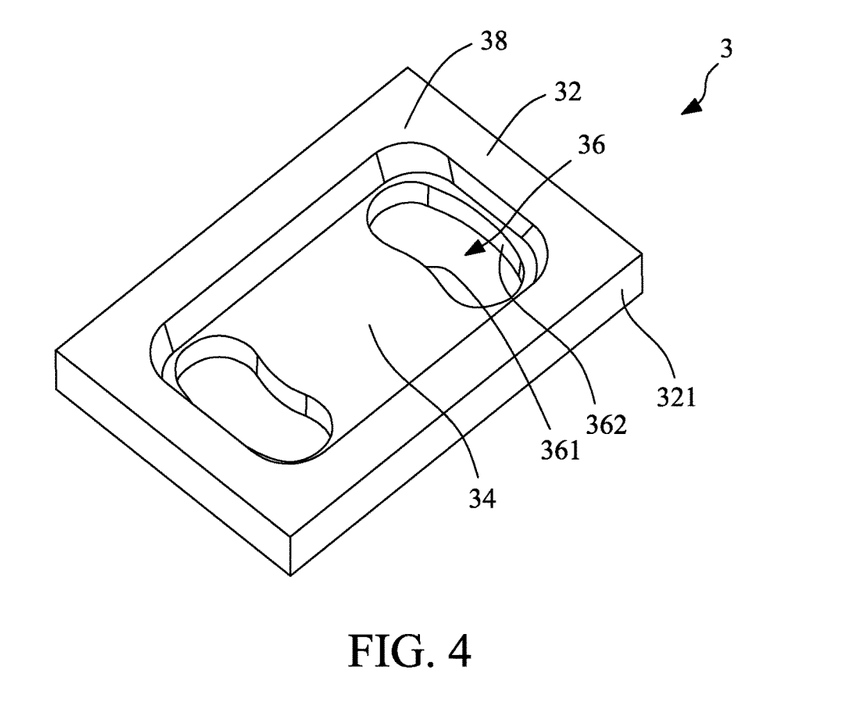
FIG. 4 illustrates a bottom perspective view of a covering structure depicted in FIGS. 1 and 2 according to one or more embodiments of the present disclosure.

FIG. 4 illustrates a bottom perspective view of the covering structure 3 depicted in FIGS. 1 and 2 according to one or more embodiments of the present disclosure. As shown in FIG. 4, the covering structure 3 can have four supporting walls 32, and a curved chamber portion 38 between each two supporting walls 32. This can help to facilitate manufacturing of the covering structure 3. The curved chamber portion 38 can be disposed at a corner of the covering structure 3.

Figure 5:
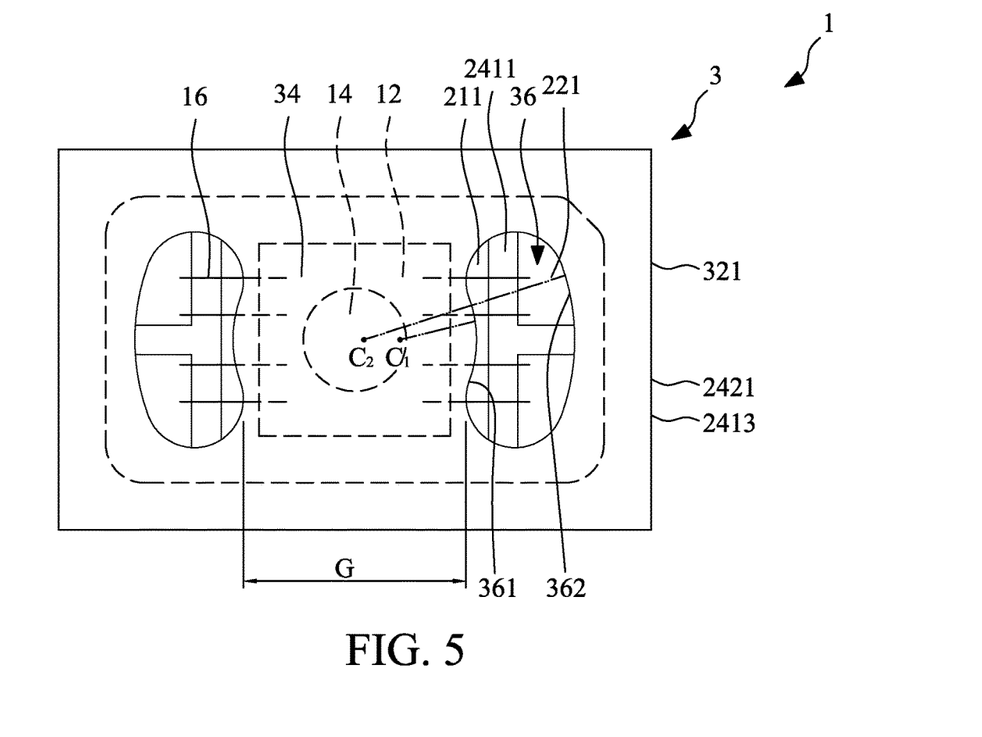
FIG. 5 illustrates a top view of the electronic device depicted in FIG. 1 according to one or more embodiments of the present disclosure.

FIG. 5 illustrates a top view of the electronic device 1 depicted in FIG. 1. As shown in FIG. 5, the electronic device 1 can be substantially rectangular from a top view. The main body 30 of the covering structure 3 can also be substantially rectangular from a top view. However, in some embodiments, the electronic device 1 or the main body 30 of the covering structure 3 may have a different shape from a top view, such as elliptical. As also shown in FIG. 5, an aperture 36 can have differently-shaped borders. In the example of FIG. 5, the apertures 36 each have a convex border and a concave border (e.g., a kidney shape), and a first curvature of the first curved surface 361 is greater than a second curvature of the second curved surface 362. More generally, the first curvature of the first curved surface 361 can be different than the second curvature of the second curved surface 362. In addition, a first center $C_1$ of the first curvature of the first curved surface 361 can be at a different location than a second center $C_2$ of the second curvature of the second curved surface 362. That is, the first center $C_1$ of the first curvature and the second center $C_2$ of the second curvature can be different points, and a distance lies between the first center $C_1$ of the first curvature of the first curved surface 361 and the second center $C_2$ of the second curvature of the second curved surface 362. In one or more embodiments, the first center $C_1$ of the first curvature is located between the first curved surface 361 and the second center $C_2$ of the second curvature.

The shape of the aperture 36 (e.g., the kidney shape of FIG. 5) can correspond to a large aperture space. This configuration may reduce manufacturing complexity as compared to other shapes. In addition, path lengths of gas entering into the accommodating space 10 and to the sensing area 14 can be substantially equal across a width of the sensing area 14, which can result in high reaction efficiency of the sensing area 14. In addition, a gap G can be between two apertures 36, and a minimum width of the gap can be greater than or equal to approximately 0.1 mm, which can facilitate manufacturing of the covering structure 3.

Figure 6:
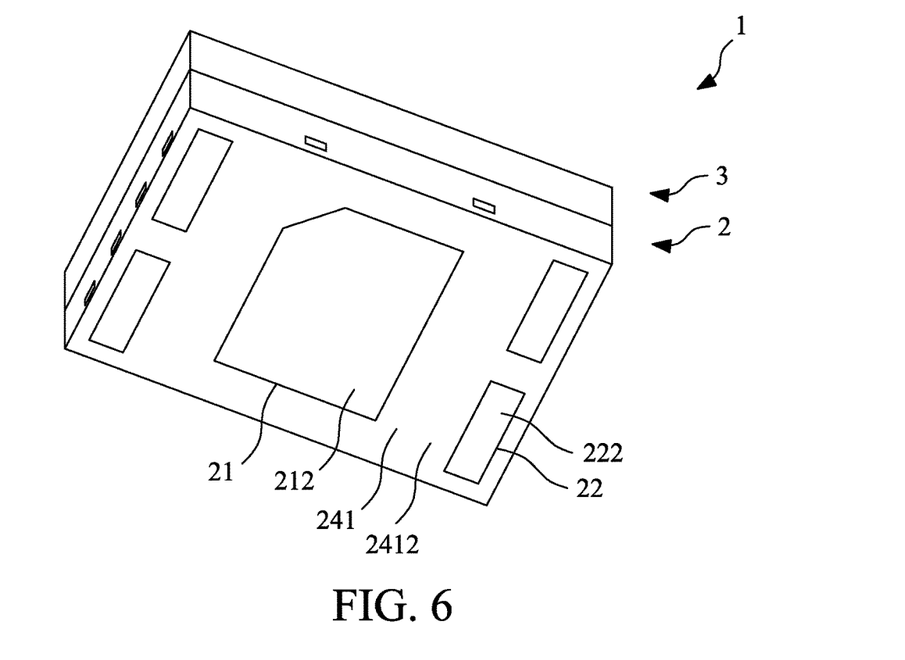
FIG. 6 illustrates a bottom perspective view of the electronic device depicted in FIG. 1 according to one or more embodiments of the present disclosure.

FIG. 6 illustrates a bottom perspective view of the electronic device 1 of FIG. 1. As shown in FIG. 6, the second surface 212 of the die paddle 21 and the second surfaces 222 of the leads 22 can be exposed from the second surface 2412 of the first portion 241 of the encapsulant 24 (e.g., for external connection).

Figure 7:
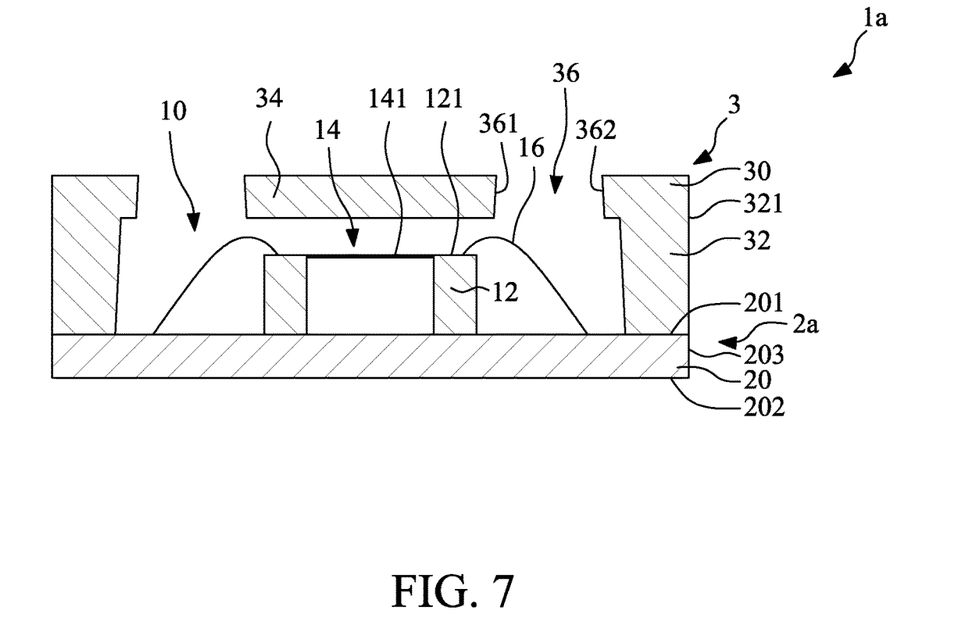
FIG. 7 illustrates a cross-sectional view of an electronic device according to one or more embodiments of the present disclosure.

FIG. 7 illustrates a cross-sectional view of an electronic device 1a according to one or more embodiments of the present disclosure. The electronic device 1a is similar in some ways to the electronic device 1 shown in FIG. 2, and same-numbered components are not further described. In FIG. 7, a carrier 2a can include a substrate 20 (such as organic substrate, inorganic substrate or ceramic substrate) that can receive the transducer 12, and can have a first surface 201, a second surface 202 opposite to the first surface, and an outermost peripheral surface 203 extending between the first surface 201 and the second surface 202. The one or more bonding wires 16 can be bonded to the first surface 201 of the carrier 2a, and the supporting wall 32 of the covering structure 3 can be attached to the first surface 201 of the carrier 2a. In addition, the outermost peripheral surface 321 of the covering structure 3 can be substantially coplanar with the outermost peripheral surface 203 of the carrier 2a. The accommodating space 10 can be defined by the supporting wall 32 of the covering structure 3.

Figure 8:
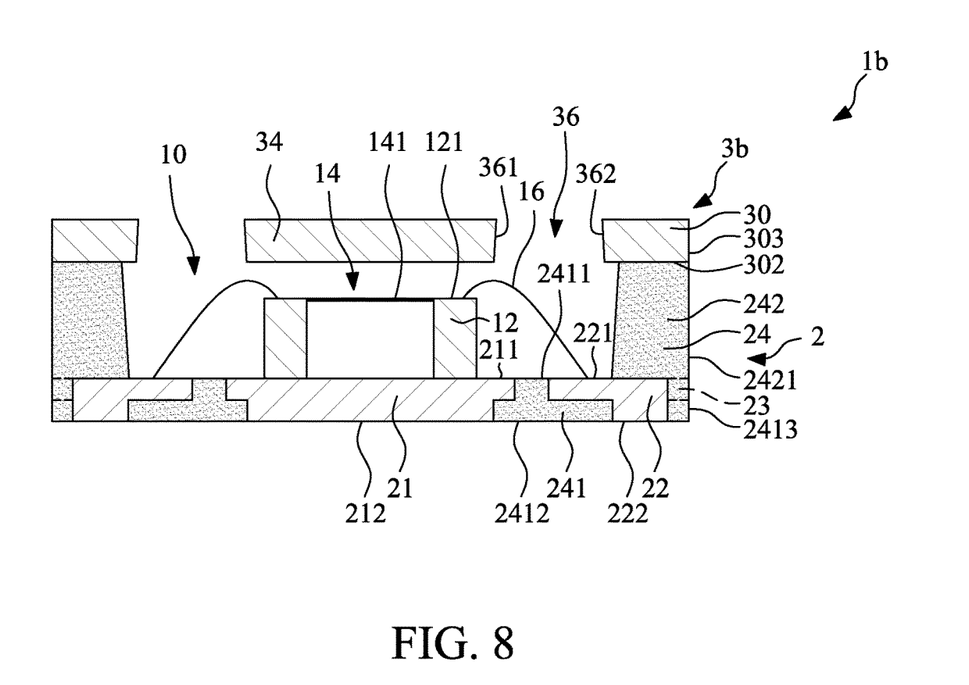
FIG. 8 illustrates a cross-sectional view of an electronic device according to one or more embodiments of the present disclosure.

FIG. 8 illustrates a cross-sectional view of an electronic device 1b according to one or more embodiments of the present disclosure. The electronic device 1b is similar in some ways to the electronic device 1 shown in FIG. 2, and same-numbered components are not further described. In FIG. 8, a covering structure 3b can be a plate with a uniform thickness, and can have a second surface 302 and an outermost peripheral surface 303. The second portion 242 (the supporting wall) of the encapsulant 24 can extend above the highest portion of the bonding wires 16, and can be attached to the second surface 302 so as to support the covering structure 3. In addition, the outermost peripheral surface 303 of the covering structure 3b can be substantially coplanar with the outer surface 2413 of the first portion 241 of the encapsulant 24 and the outer surface 2421 of the second portion 242 (the supporting wall) of the carrier 2. The accommodating space 10 can be defined by the second portion 242 of the carrier 2.

Figure 9:
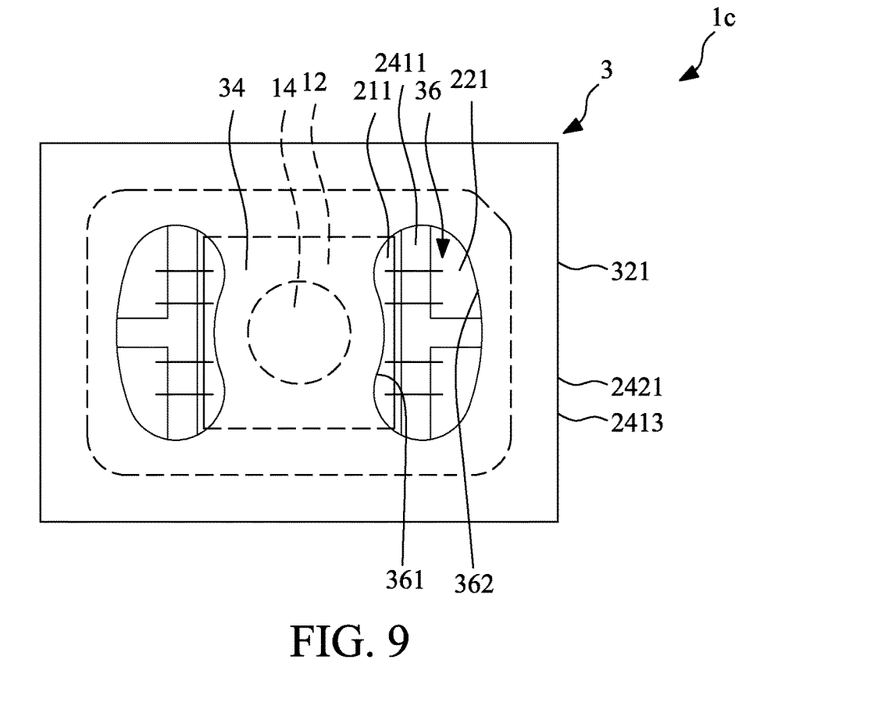
FIG. 9 illustrates a top view of an electronic device according to one or more embodiments of the present disclosure.

FIG. 9 illustrates a top view of an electronic device 1c according to one or more embodiments of the present disclosure. The electronic device 1c is similar in some ways to the electronic device 1 shown in FIG. 5, and same-numbered components are not further described. In FIG. 9, the apertures 36 are closer to each other than the apertures 36 of the electronic device 1 in FIG. 5, such that an overall size (e.g., surface area or total volume) of the electronic device 1c is less than a corresponding size of the electronic device 1. In FIG. 9, a portion of each of the apertures 36 is disposed above a portion of the transducer 12, such that the portion of the transducer 12 is exposed from the top view. That is, the shelter portion 34 of the covering structure 3 might not fully cover the entire transducer 12.

Figure 10:
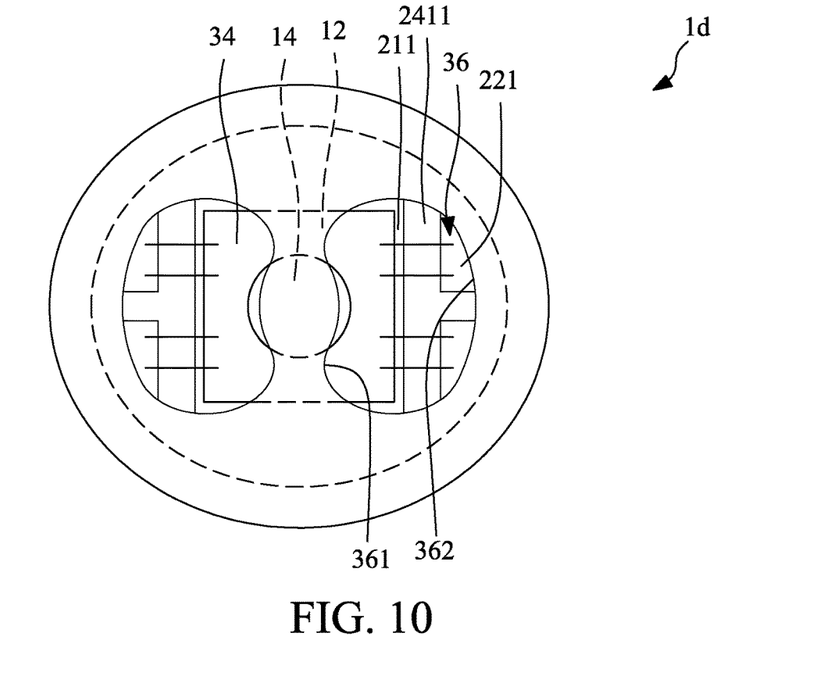
FIG. 10 illustrates a top view of an electronic device according to one or more embodiments of the present disclosure.

FIG. 10 illustrates a top view of an electronic device 1d according to one or more embodiments of the present disclosure. The electronic device 1d is similar in some ways to the electronic device 1c shown in FIG. 9, and same-numbered components are not further described. In FIG. 10, the apertures 36 are closer to each other than the apertures 36 of the electronic device 1c depicted in FIG. 9, such that a size of the electronic device 1d is smaller than a corresponding size of the electronic device 1c. As shown in FIG. 10, a portion of each of the apertures 36 can be disposed above a portion of the transducer 12 and a portion of the sensing area 14 such that the portion of the transducer 12 and the portion of the sensing area 14 are exposed from the top view. That is, the shelter portion 34 of the covering structure 3 might not fully cover the entire transducer 12 and the entire sensing area 14. Additionally, by way of non-limiting illustration, FIG. 10 illustrates that the electronic device 1d and the main body 30 of the covering structure 3 can be substantially circular from a top view.

Figure 11:
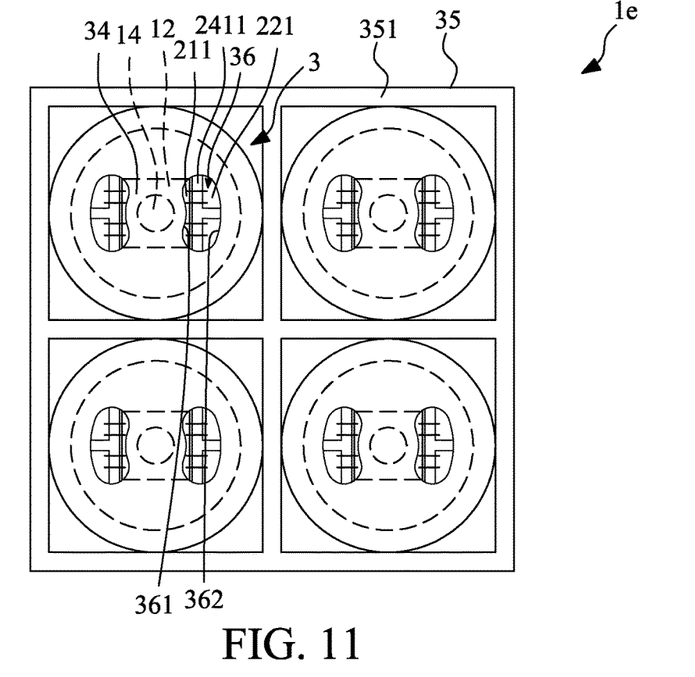
FIG. 11 illustrates a top view of an electronic device according to one or more embodiments of the present disclosure.

FIG. 11 illustrates a top view of an electronic device 1e according to one or more embodiments of the present disclosure. The electronic device 1e is similar in some ways to the electronic device 1c shown in FIG. 9, and same-numbered components are not further described. In FIG. 11, the electronic device 1e includes four transducers 12, with a corresponding four covering structures 3 and a frame 35. The frame 35 can include a plurality of connecting bars 351 that cross each other. A periphery of each of the covering structures 3 can connect four connecting bars 351. Additionally, the main body 30 of each covering structure 3 is shown by way of non-limiting example as substantially circular from a top view.

Figure 12:
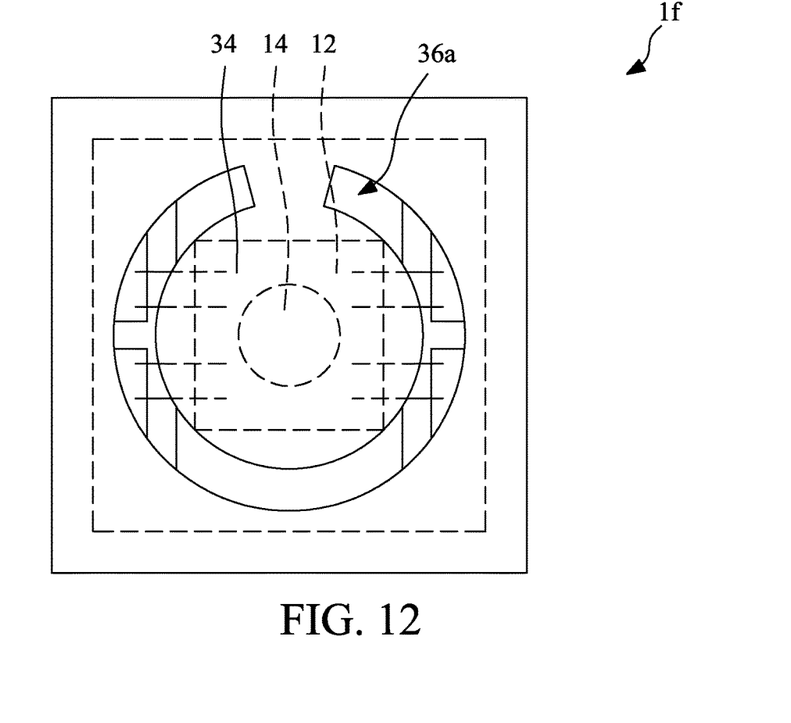
FIG. 12 illustrates a top view of an electronic device according to one or more embodiments of the present disclosure.

FIG. 12 illustrates a top view of an electronic device if according to one or more embodiments of the present disclosure. The electronic device if is similar in some ways to the electronic device 1 shown in FIG. 5, and same-numbered components are not further described. In FIG. 12, an aperture 36a has a different shape as compared to the apertures 36 depicted in FIG. 5 and described above. As shown in FIG. 12, the covering structure 3 can include one aperture 36 with a shape of a portion of an annular ring.

Figure 13:
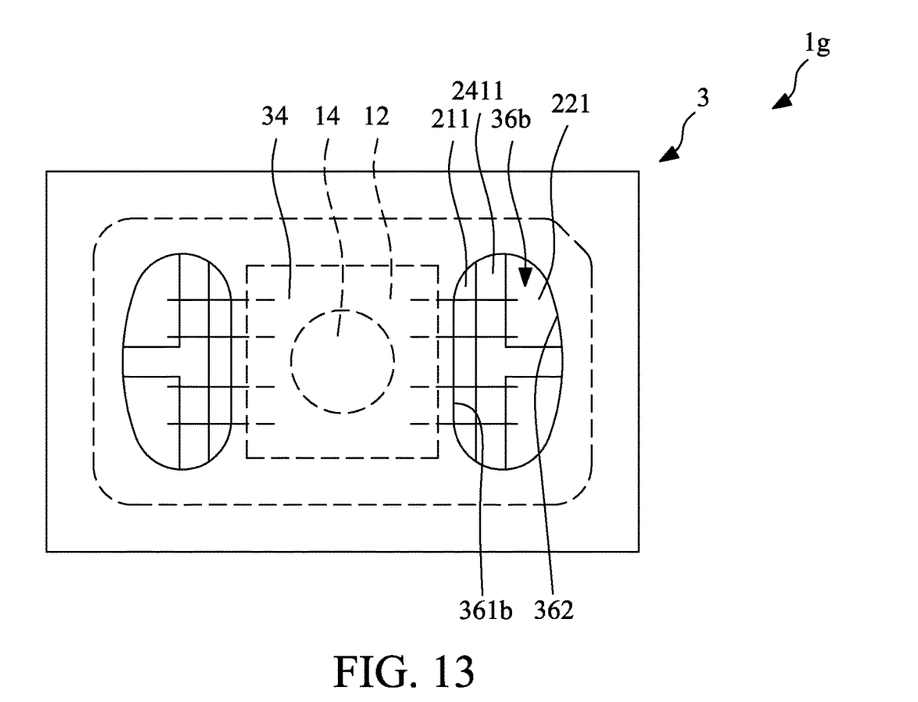
FIG. 13 illustrates a top view of an electronic device according to one or more embodiments of the present disclosure.

FIG. 13 illustrates a top view of an electronic device 1g according to one or more embodiments of the present disclosure. The electronic device 1g is similar in some ways to the electronic device 1 shown in FIG. 5, and same-numbered components are not further described. In FIG. 13, a first surface 361b of an aperture 36b of the electronic device 1g can be a substantially flat surface rather than a curved surface.

Figure 14:
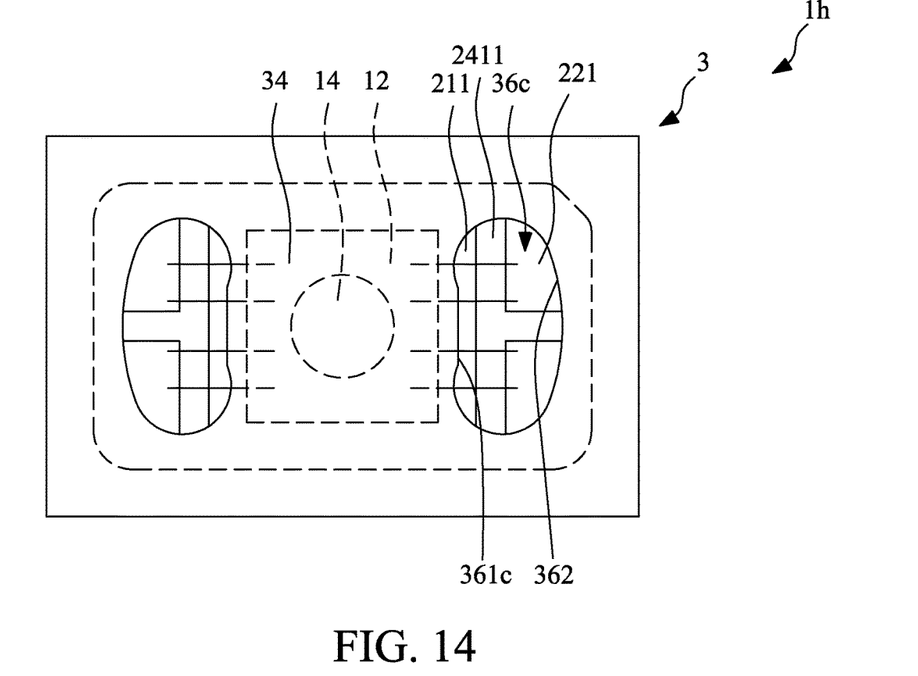
FIG. 14 illustrates a top view of an electronic device according to one or more embodiments of the present disclosure.

FIG. 14 illustrates a top view of an electronic device 1h according to one or more embodiments of the present disclosure. The electronic device 1h is similar in some ways to the electronic device 1g shown in FIG. 13, and same-numbered components are not further described. In FIG. 14, a first surface 361c of an aperture 36c of the electronic device 1h can be a substantially flat surface with curved ends.

Figure 15:
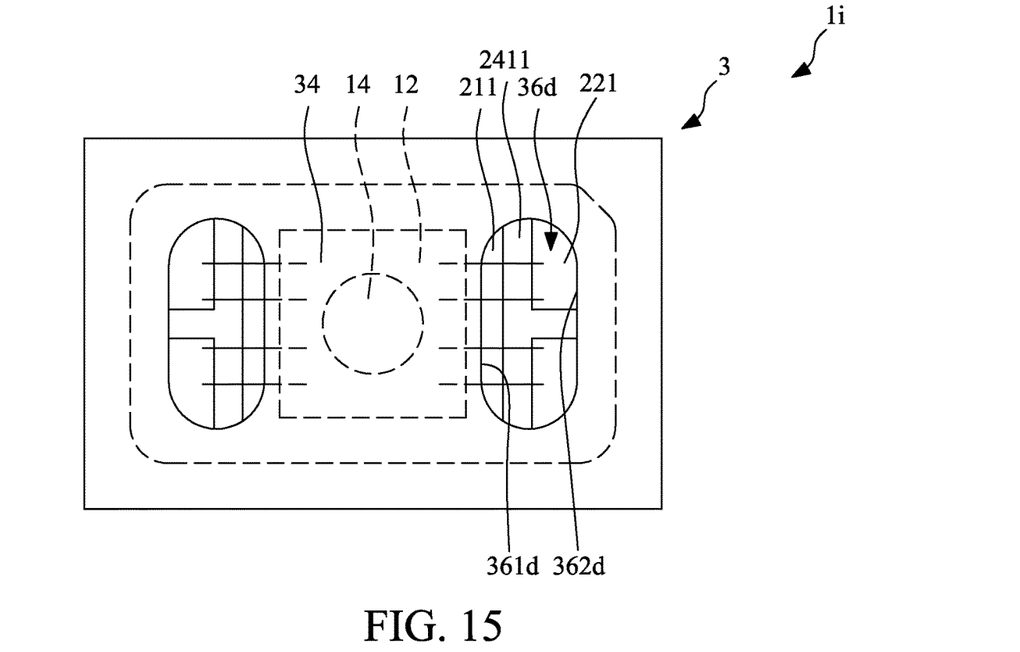
FIG. 15 illustrates a top view of an electronic device according to one or more embodiments of the present disclosure.

FIG. 15 illustrates a top view of an electronic device 1i according to one or more embodiments of the present disclosure. The electronic device 1i is similar in some ways to the electronic device 1g shown in FIG. 13, and same-numbered components are not further described. In FIG. 15, a first surface 361d and a second surface 362d of an aperture 36d of the electronic device 1i in FIG. 15 are substantially flat surfaces rather than curved. As shown in FIG. 15, the second surface 362d can be substantially parallel with the first surface 361d.

Figure 16:
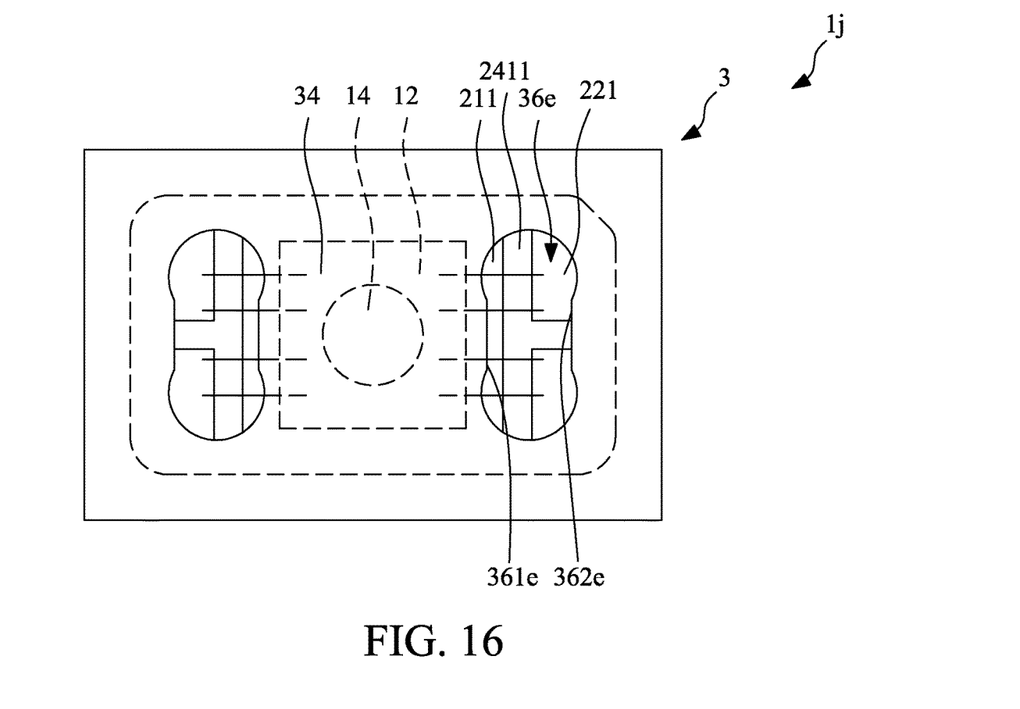
FIG. 16 illustrates a top view of an electronic device according to one or more embodiments of the present disclosure.
Figure 17:
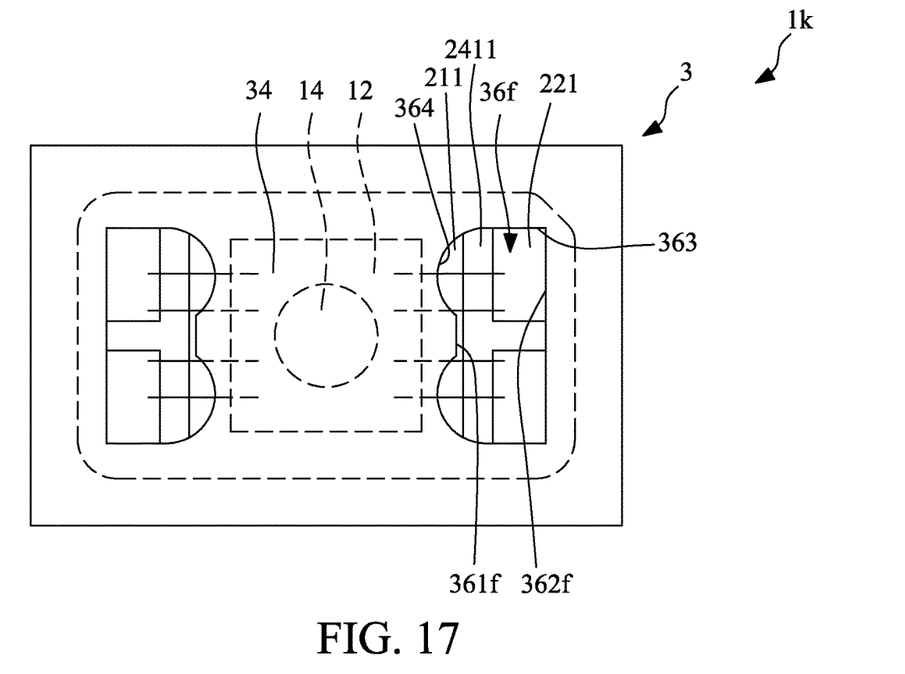
FIG. 17 illustrates a top view of an electronic device according to one or more embodiments of the present disclosure.

FIG. 16 illustrates a top view of an electronic device 1j according to one or more embodiments of the present disclosure. The electronic device 1j is similar in some ways to the electronic device 1i shown in FIG. 15, and same-numbered components are not further described. In FIG. 16, a first surface 361e and a second surface 362e of an aperture 36e of the electronic device 1j can each be a substantially flat surface with curved ends FIG. 17 illustrates a top view of an electronic device 1k according to one or more embodiments of the present disclosure. The electronic device 1k is similar in some ways to the electronic device 1i shown in FIG. 15, and same-numbered components are not further described. In FIG. 17, an aperture 36f includes two third surfaces 363 and two fourth surfaces 364 in addition to a first surface 361f and a second surface 362f. The third surface 363 can be substantially perpendicular to the second surface 362f. The fourth surface 364 can be a curved surface and can connect the first surface 361f and the third surface 363. As shown in FIG. 17, the fourth surface 364 can be substantially a semicircle and the aperture 36f can define substantially a B-shaped perimeter.

Figure 18:
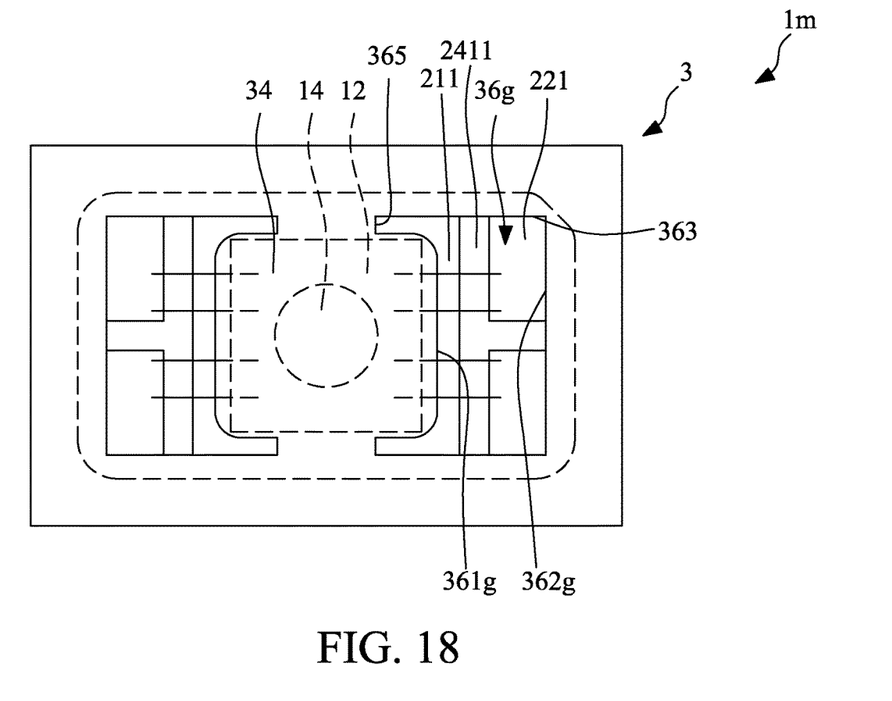
FIG. 18 illustrates a top view of an electronic device according to one or more embodiments of the present disclosure.

FIG. 18 illustrates a top view of an electronic device 1m according to one or more embodiments of the present disclosure. The electronic device 1m is similar in some ways to the electronic device 1k shown in FIG. 17, and same-numbered components are not further described. In FIG. 18, an aperture 36 further includes a fifth surface 365 in addition to a first surface 361g and second surface 362g. The fifth surface 365 can be substantially perpendicular to the third surface 363, and can be substantially parallel to the second surface 362g. The fifth surface 365 can connect the first surface 361g and the third surface 363. As shown in FIG. 18, the first surface 361g of the aperture 36g can be substantially in a U shape.

Figure 19:
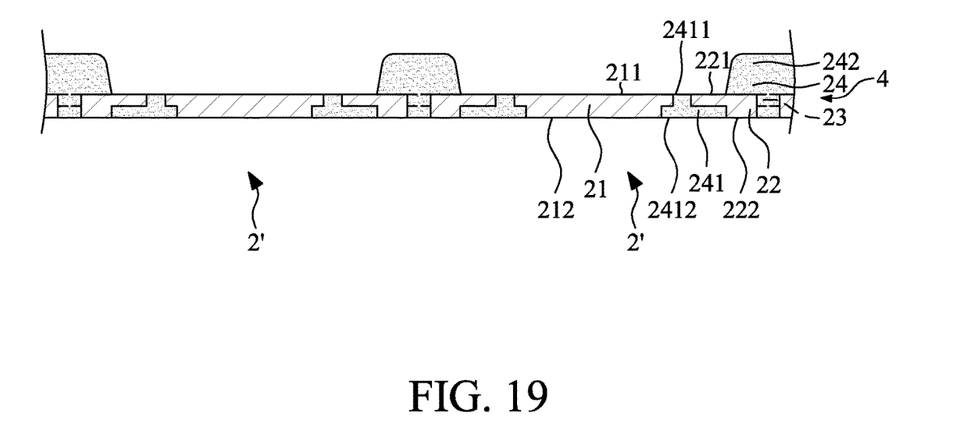
FIG. 19, FIG. 20, FIG. 21, FIG. 22, FIG. 23 and FIG. 24 illustrate a method for manufacturing an electronic device according to one or more embodiments of the present disclosure.

FIGS. 19 to 24 illustrate a method for manufacturing an electronic device according to one or more embodiments of the present disclosure. Referring to FIG. 19, a carrier strip 4 is provided. The carrier strip 4 can include a plurality of carrier units 2'. Each of the carrier units 2' can be similar to the carrier 2 shown in FIG. 2. The carrier units 2' can be connected to each other by connecting bars 23.

Figure 20:
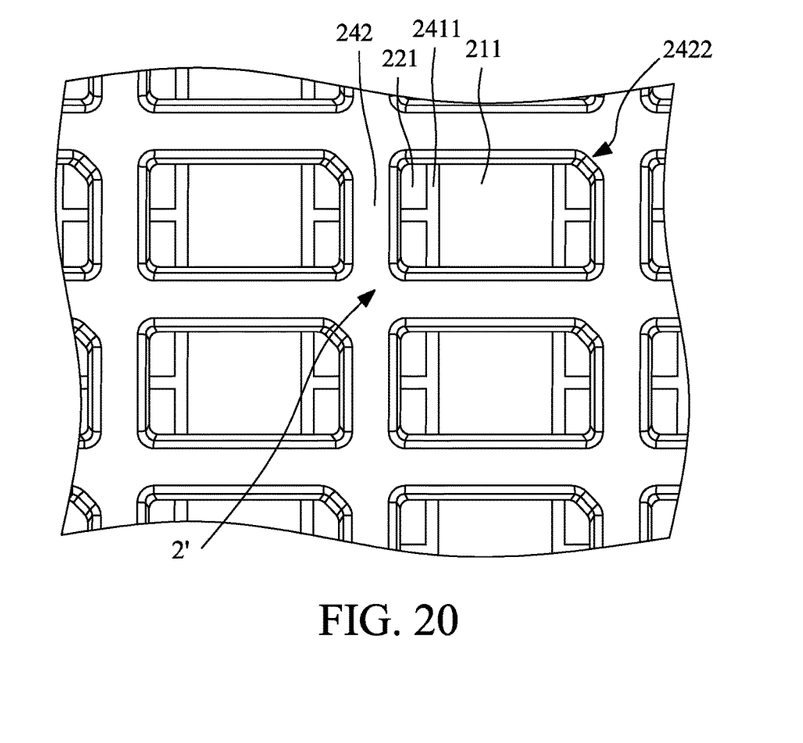

Referring to FIG. 20, a top view of the carrier strip 4 is shown. The carrier units 2' can be arranged in an array. In a carrier unit 2', a corner 2422 of a second portion 242 of an encapsulant 24 can be different than other corners, such as having a flat portion, and the corner 2422 may be used for positioning.

Figure 21:
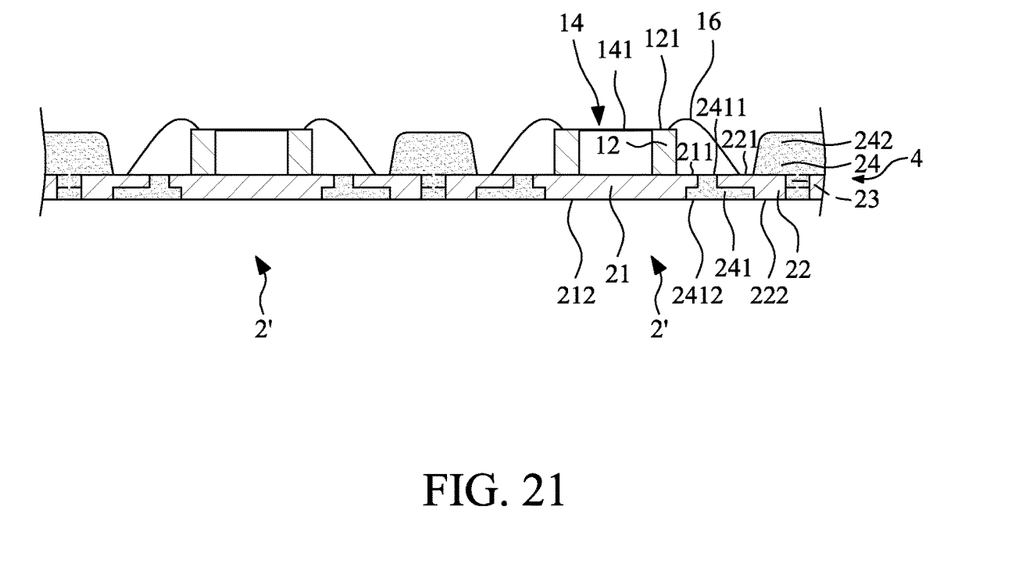

Referring to FIG. 21, transducers 12 are disposed on the carrier units 2'. It is noted that there may be one transducer 12 on one carrier unit 2', or multiple (e.g., four) transducers 12 on one carrier unit 2'. Then, the transducer(s) 12 can be electrically connected to the carrier unit 2' by bonding wires 16.

Figure 22:
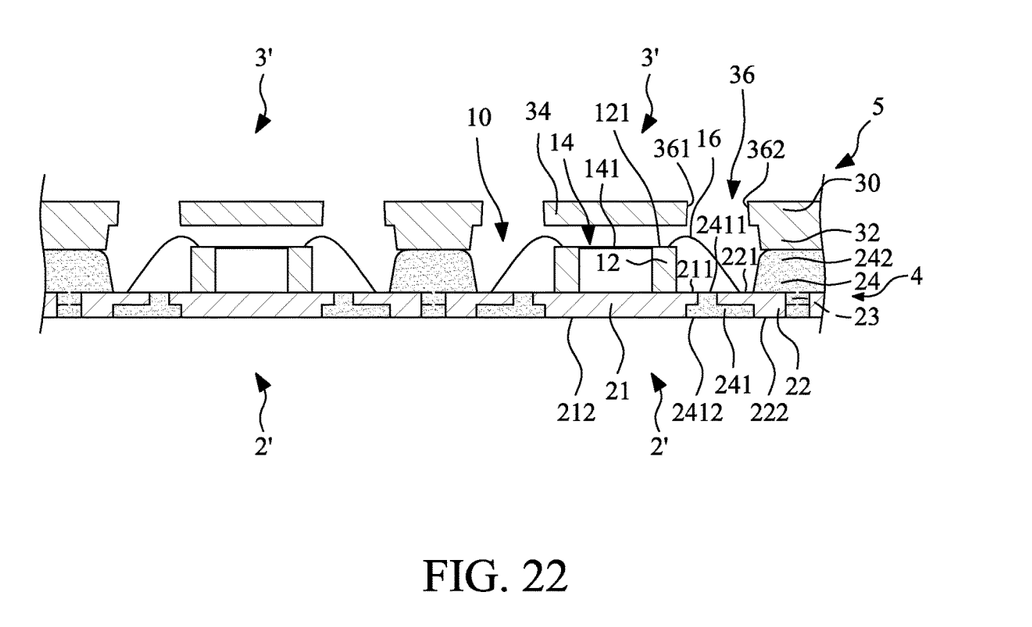

Referring to FIG. 22, a covering structure strip 5 is attached (e.g., adhered) to the carrier strip 4. The covering structure strip 5 includes covering structure units 3' arranged in an array. Each of the covering structure units 3' can be similar to the covering structure 3 shown in FIG. 2. In one or more embodiments, the covering structure strip 5 may be formed by injection molding. Supporting walls 32 of the covering structure units 3' can be attached to the second portion 242 (supporting wall) of the encapsulant 24 of the carrier units 2'.

Figure 23:
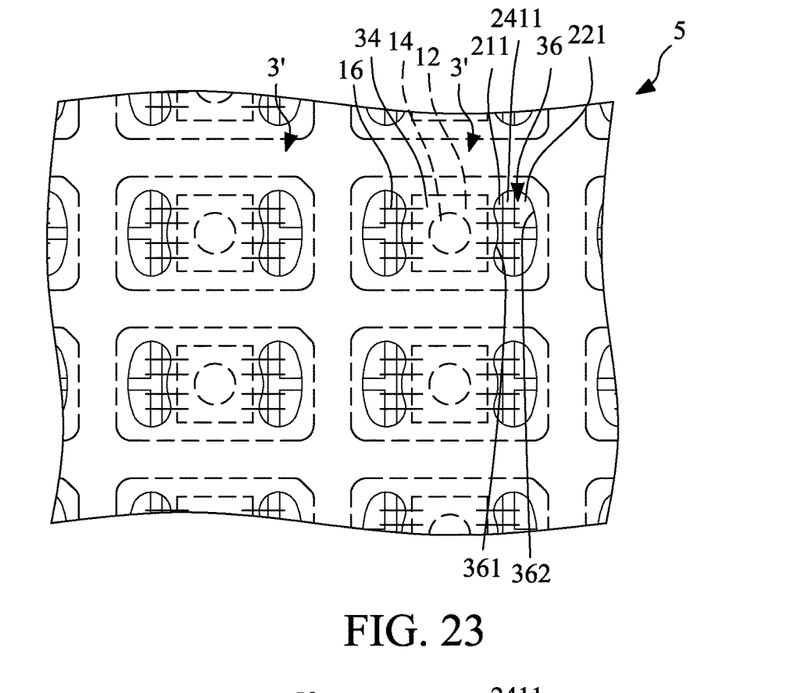

Referring to FIG. 23, a top view of the covering structure strip 5 attached on the carrier strip 4 is shown. The covering structure units 3' can be arranged in an array.

Figure 24:
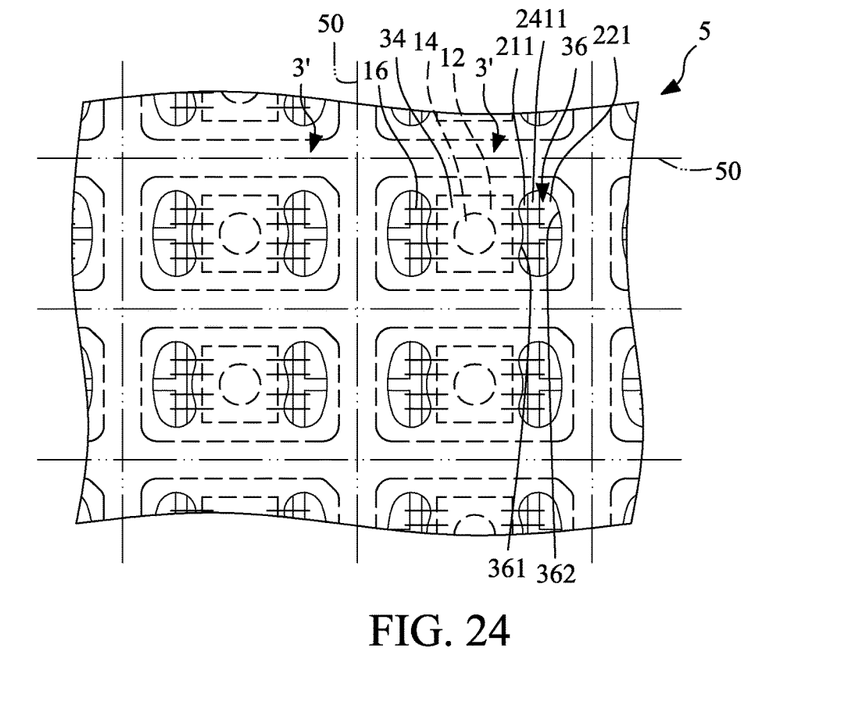

Referring to FIG. 24, a singulation process can be conducted to obtain multiple electronic devices 1, such as those devices shown in FIG. 1. In one embodiment, the singulation process can be conducted by cutting (e.g., blade cutting or laser cutting) along cutting lines 50. The covering structure strip 5 and the carrier strip 4 can be cut together (e.g., in a continuous cutting motion vertically) along the cutting lines 50, such that, as shown in the example of FIGS. 1 and 2, the outer surface 321 of the supporting wall 32 can be substantially coplanar with the outer surface 2413 of the first portion 241 of the encapsulant 24 and the outer surface 2421 of the second portion 242 (the supporting wall) of the encapsulant 24 (the outermost peripheral surface of the carrier 2).

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of embodiments of this disclosure are not deviated by such arrangement.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Two surfaces can be deemed to be coplanar or substantially coplanar if a displacement between the two surfaces is no greater than 5 μm, no greater than 2 μm, no greater than 1 μm, or no greater than 0.5 μm. The term "substantially parallel" with respect to two edges or surfaces can refer to lying along a line or along a plane, with an angular displacement between the two edges or surfaces being less than or equal to 10°, such as less than or equal to 5°, less than or equal to 3°, less than or equal to 2°, or less than or equal to 1°. The term "substantially perpendicular" referring to two components can refer to a range of variation of less than or equal to ±10° of 90° between the two components, such as less than or equal to ±5°, less than or equal to ±3°, less than or equal to ±2°, or less than or equal to ±1°.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. An electronic device, comprising:
    a transducer comprising a sensing area; and
    a covering structure that covers the transducer, wherein the covering structure comprises a shelter portion and defines at least one aperture, the shelter portion covers the sensing area, the aperture includes a first curved surface and a second curved surface farther away from the sensing area than the first curved surface, and a first center of a first curvature of the first curved surface is at a different location than a second center of a second curvature of the second curved surface;
    wherein the first center of the first curvature is located between the first curved surface and the second center of the second curvature.

2. The electronic device according to claim 1, wherein the first curvature of the first curved surface is greater than the second curvature of the second curved surface.

3. The electronic device according to claim 1, wherein the covering structure is rectangular from a top view.

4. The electronic device according to claim 1, wherein the at least one aperture of the covering structure includes a first aperture on a first side of the shelter portion and a second aperture on a second side of the shelter portion, and the first and the second apertures are substantially symmetrical to each other.

5. The electronic device according to claim 4, wherein a gap greater than or equal to approximately 0.1 mm separates the first and the second apertures.

6. The electronic device according to claim 1, wherein the covering structure further comprises at least two supporting walls and a curved chamber portion between the two supporting walls.

7. The electronic device according to claim 6, wherein a thickness of at least one of the supporting walls is greater than or equal to approximately 0.1 mm.

8. The electronic device according to claim 1, further comprising a substrate and the transducer is disposed over the substrate, wherein the covering structure further covers the substrate, and an outermost peripheral surface of the covering structure is substantially coplanar with an outermost peripheral surface of the substrate.

9. The electronic device according to claim 8, wherein the covering structure is a plate, and the substrate comprises at least one supporting wall supporting the covering structure.

10. The electronic device according to claim 1, wherein lengths of gas paths from entering through the aperture to reaching the sensing area are substantially equal across a width of the sensing area.

11. A lid structure, comprising:
a main body including a shelter portion and defining at least one aperture surrounding the shelter portion, each aperture of the at least one aperture having a first surface and a second surface opposite to the first surface, and a first center of a first curvature of the first surface is at a different location than a second center of a second curvature of the second surface;
wherein the first center of the first curvature is located between the first curved surface and the second center of the second curvature.

12. The lid structure according to claim 11, wherein the first curvature of the first surface is greater than the second curvature of the second surface.

13. The lid structure according to claim 11, wherein the main body is rectangular from a top view.

14. The lid structure according to claim 11, wherein the at least one aperture includes a first aperture and a second aperture, and the first surfaces of the first and the second apertures define a portion of the shelter portion.

15. The lid structure according to claim 11, wherein a material of the main body is a plastic.

16. The lid structure according to claim 11, further comprising at least one supporting wall extending vertically from a periphery of the main body.

17. A package structure, comprising:
a carrier;
a die including a sensing area disposed adjacent to a surface of the die; and
a covering structure attached to the carrier forming an accommodating space that accommodates the die, wherein the covering structure includes a shelter portion and defines at least one aperture, the shelter portion covers the sensing area, the aperture includes a first curved surface and a second curved surface farther away from the sensing area than the first curved surface, and a first curvature of the first curved surface is greater than a second curvature of the second curved surface.

18. The package structure according to claim 17, wherein the at least one aperture includes a first aperture at a first side of the shelter portion and a second aperture at a second side of the shelter portion, and the first and the second apertures are substantially symmetrical to each other.

19. The package structure according to claim 17, wherein an outermost peripheral surface of the covering structure is substantially coplanar with an outermost peripheral surface of the carrier.

20. The package structure according to claim 17, wherein the covering structure further comprises at least two supporting walls attached to the carrier and a curved chamber portion between the two supporting walls.

21. The package structure according to claim 17, wherein the covering structure is a plate, and the carrier comprises at least one supporting wall supporting the covering structure.

\* \* \* \* \*